US008493216B2

(12) United States Patent
Angell et al.

(10) Patent No.: US 8,493,216 B2
(45) Date of Patent: Jul. 23, 2013

(54) GENERATING DEPORTMENT AND COMPORTMENT COHORTS

(75) Inventors: Robert Lee Angell, Salt Lake City, UT (US); Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 840 days.

(21) Appl. No.: 12/336,471

(22) Filed: Dec. 16, 2008

(65) Prior Publication Data
US 2010/0148970 A1 Jun. 17, 2010

(51) Int. Cl.
G08B 23/00 (2006.01)

(52) U.S. Cl.
USPC ........ 340/573.1; 382/115; 382/116; 382/118; 706/52; 706/54; 707/736; 707/E17.001; 707/E17.143; 707/705

(58) Field of Classification Search
USPC .... 340/573.1; 382/115; 706/52, 54; 707/705, 707/736, E17.001, E17.143
See application file for complete search history.

(56) References Cited

U.S. PATENT DOCUMENTS

| | | | |
|---|---|---|---|
| 4,742,388 A | 5/1988 | Cooper et al. | |
| 5,664,109 A | 9/1997 | Johnson et al. | |
| 5,774,569 A | 6/1998 | Waldenmaier | |
| 6,054,928 A * | 4/2000 | Lemelson et al. | 340/573.4 |
| 6,178,141 B1 | 1/2001 | Duckworth et al. | |
| 6,242,186 B1 | 6/2001 | Salonen | |
| 6,553,336 B1 | 4/2003 | Johnson et al. | |
| 6,646,676 B1 | 11/2003 | DaGraca et al. | |
| 6,795,808 B1 * | 9/2004 | Strubbe et al. | 704/275 |
| 7,308,385 B2 | 12/2007 | Wegerich et al. | |
| 7,363,309 B1 | 4/2008 | Waite et al. | |
| 7,538,658 B2 | 5/2009 | Twitchell, Jr. | |

(Continued)

FOREIGN PATENT DOCUMENTS
KR 20080082924 A 9/2008

OTHER PUBLICATIONS

U.S. Appl. No. 12/333,311, Angell et al., Final Office Action Mailed Aug. 18, 2011.

(Continued)

*Primary Examiner* — George Bugg
*Assistant Examiner* — Naomi Small
(74) *Attorney, Agent, or Firm* — John R. Pivnichny; Law Office of Jim Boice

(57) ABSTRACT

A computer implemented method, apparatus, and computer program product for generating deportment and comportment cohorts. Digital sensor data associated with an individual is received. The digital sensor data comprises event metadata describing a set of events associated with the individual. The set of events comprises at least one of body language, facial expressions, vocalizations, and social interactions of the individual. In response to determining description data for the individual is available, the description data is retrieved. The description data comprises at least one of identification information, past history information, and current status information for the individual. A set of conduct analysis models based on the event metadata and the available description data is selected. The set of conduct analysis models process the event metadata describing the set of events associated with the individual to identify and interpret the set of events. The event metadata and the description data is analyzed in the set of conduct analysis models to form a deportment and comportment cohort. The deportment and comportment cohort comprises attributes identifying a demeanor and manner of the individual.

20 Claims, 5 Drawing Sheets

U.S. PATENT DOCUMENTS

| | | | |
|---|---|---|---|
| 7,548,874 B2 | 6/2009 | Kanevsky et al. | |
| 7,584,280 B2 | 9/2009 | Kim et al. | |
| 7,667,596 B2 | 2/2010 | Ozdemir et al. | |
| 7,683,929 B2 | 3/2010 | Elazar et al. | |
| 7,755,480 B2 | 7/2010 | Aritsuka et al. | |
| 7,840,515 B2 | 11/2010 | Ozdemir et al. | |
| 7,840,897 B2 * | 11/2010 | Ancier | 715/719 |
| 7,846,020 B2 | 12/2010 | Walker et al. | |
| 7,921,036 B1 | 4/2011 | Sharma et al. | |
| 7,930,204 B1 | 4/2011 | Sharma et al. | |
| 7,953,686 B2 | 5/2011 | Angell et al. | |
| 7,974,869 B1 | 7/2011 | Sharma et al. | |
| 8,000,777 B2 | 8/2011 | Jaeb et al. | |
| 2002/0176604 A1 | 11/2002 | Shekhar et al. | |
| 2002/0183971 A1 | 12/2002 | Wegerich et al. | |
| 2002/0194117 A1 | 12/2002 | Nabe et al. | |
| 2003/0023612 A1 | 1/2003 | Carlbom et al. | |
| 2003/0036903 A1 | 2/2003 | Konopka et al. | |
| 2003/0088463 A1 | 5/2003 | Kanevsky et al. | |
| 2003/0131362 A1 | 7/2003 | Jasinschi et al. | |
| 2003/0169907 A1 | 9/2003 | Edwards et al. | |
| 2003/0174773 A1 | 9/2003 | Comaniciu et al. | |
| 2003/0231769 A1 | 12/2003 | Bolle et al. | |
| 2004/0064341 A1 | 4/2004 | Langan et al. | |
| 2004/0095617 A1 | 5/2004 | Mangerson | |
| 2004/0161133 A1 | 8/2004 | Elazar et al. | |
| 2004/0181376 A1 * | 9/2004 | Fables et al. | 703/6 |
| 2004/0225202 A1 | 11/2004 | Skinner | |
| 2004/0240542 A1 | 12/2004 | Yeredor et al. | |
| 2004/0249650 A1 * | 12/2004 | Freedman et al. | 705/1 |
| 2005/0018861 A1 | 1/2005 | Tashev | |
| 2005/0043060 A1 | 2/2005 | Brandenberg et al. | |
| 2005/0125325 A1 | 6/2005 | Chai et al. | |
| 2005/0169367 A1 | 8/2005 | Venetianer et al. | |
| 2005/0187437 A1 * | 8/2005 | Matsugu et al. | 600/301 |
| 2005/0216273 A1 * | 9/2005 | Reding et al. | 704/275 |
| 2006/0000420 A1 | 1/2006 | Davies | |
| 2006/0004582 A1 | 1/2006 | Claudatos et al. | |
| 2006/0111961 A1 | 5/2006 | McQuivey | |
| 2006/0206379 A1 | 9/2006 | Rosenberg | |
| 2006/0251339 A1 | 11/2006 | Gokturk et al. | |
| 2007/0013776 A1 | 1/2007 | Venetianer et al. | |
| 2007/0122003 A1 * | 5/2007 | Dobkin et al. | 382/115 |
| 2007/0225577 A1 * | 9/2007 | Mathan | 600/301 |
| 2007/0230270 A1 | 10/2007 | Calhoun | |
| 2008/0004793 A1 | 1/2008 | Horvitz et al. | |
| 2008/0004951 A1 | 1/2008 | Huang et al. | |
| 2008/0024299 A1 * | 1/2008 | Robertson | 340/572.1 |
| 2008/0031491 A1 | 2/2008 | Ma et al. | |
| 2008/0055049 A1 | 3/2008 | Weill et al. | |
| 2008/0067244 A1 | 3/2008 | Marks | |
| 2008/0071162 A1 | 3/2008 | Jaeb et al. | |
| 2008/0082399 A1 | 4/2008 | Noble et al. | |
| 2008/0092245 A1 * | 4/2008 | Alward et al. | 726/28 |
| 2008/0098456 A1 * | 4/2008 | Alward et al. | 726/1 |
| 2008/0109398 A1 * | 5/2008 | Harter | 707/2 |
| 2008/0228577 A1 * | 9/2008 | Decre et al. | 705/14 |
| 2008/0240496 A1 | 10/2008 | Senior | |
| 2008/0243439 A1 | 10/2008 | Runkle et al. | |
| 2008/0260212 A1 * | 10/2008 | Moskal et al. | 382/118 |
| 2008/0262743 A1 | 10/2008 | Lewis et al. | |
| 2009/0002155 A1 * | 1/2009 | Ma et al. | 340/539.25 |
| 2009/0070138 A1 | 3/2009 | Langheier et al. | |
| 2009/0092283 A1 * | 4/2009 | Whillock et al. | 382/103 |
| 2009/0109795 A1 | 4/2009 | Marti | |
| 2009/0171783 A1 | 7/2009 | Raju | |
| 2009/0185723 A1 | 7/2009 | Kurtz et al. | |
| 2009/0195401 A1 | 8/2009 | Maroney et al. | |
| 2009/0231436 A1 | 9/2009 | Faltesek et al. | |
| 2010/0008515 A1 | 1/2010 | Fulton et al. | |
| 2010/0131206 A1 | 5/2010 | Angell et al. | |
| 2010/0131263 A1 | 5/2010 | Angell et al. | |
| 2010/0131502 A1 | 5/2010 | Fordham | |
| 2010/0148970 A1 | 6/2010 | Angell et al. | |
| 2010/0150457 A1 | 6/2010 | Angell et al. | |
| 2010/0150458 A1 | 6/2010 | Angell et al. | |
| 2010/0153146 A1 | 6/2010 | Angell et al. | |
| 2010/0153147 A1 | 6/2010 | Angell et al. | |
| 2010/0153174 A1 | 6/2010 | Angell et al. | |
| 2010/0153180 A1 | 6/2010 | Angell et al. | |
| 2010/0153353 A1 | 6/2010 | Angell et al. | |
| 2010/0153389 A1 | 6/2010 | Angell et al. | |
| 2010/0153390 A1 | 6/2010 | Angell et al. | |
| 2010/0153458 A1 | 6/2010 | Angell et al. | |
| 2010/0153470 A1 | 6/2010 | Angell et al. | |
| 2010/0153597 A1 | 6/2010 | Angell et al. | |
| 2010/0177169 A1 | 7/2010 | Saric | |
| 2010/0207874 A1 * | 8/2010 | Yuxin et al. | 345/156 |

OTHER PUBLICATIONS

U.S. Appl. No. 12/333,316, Angell et al., Non-Final Office Action Mailed Sep. 6, 2011.
U.S. Appl. No. 12/336,488, Angell et al., Non-Final Office Action Mailed Sep. 15, 2011.
U.S. Appl. No. 12/333,273, Angell et al., Non-Final Office Action Mailed Sep. 30, 2011.
U.S. Appl. No. 12/335,857, Angell et al., Final Office Action Mailed Oct. 13, 2011.
U.S. Appl. No. 12/335,731, Angell et al., Non-Final Office Action Mailed Oct. 26, 2011.
U.S. Appl. No. 12/333,321, filed Dec. 12, 2008, Angell et al.
U.S. Appl. No. 12/333,323, filed Dec. 12, 2008, Angell et al.
U.S. Appl. No. 12/277,122, filed Nov. 24, 2008, Angell et al.
U.S. Appl. No. 12/333,311, filed Dec. 12, 2008, Angell et al.
U.S. Appl. No. 12/333,316, filed Dec. 12, 2008, Angell et al.
U.S. Appl. No. 12/275,830, filed Nov. 21, 2008, Angell et al.
U.S. Appl. No. 12/333,256, filed Dec. 11, 2008, Angell et al.
U.S. Appl. No. 12/335,521, filed Dec. 15, 2008, Angell et al.
Brown et al., "IBM Smart Surveillance System (S3): An Open and Extensible Architecture for Smart Video Surveillance", Retrieved on Jan. 12, 2009, pp. 1-4.
U.S. Appl. No. 12/277,122, Non-Final Office Action Mailed May 10, 2011.
U.S. Appl. No. 12/333,311, Non-Final Office Action Mailed Feb. 28, 2011.
U.S. Appl. No. 12/333,321: Non-Final Office Action Mailed May 23, 2011.
U.S. Appl. No. 12/335,521: Non-Final Office Action Mailed Jun. 27, 2011.
M. Borg et al., "Video Surveillance for Aircraft Activity Monitoring", IEEE Conference on Advanced Video and Signal Based Surveillance, 2005, pp. 16-21.
Y. Matsushita et al., "Illumination Normalization With Time-Dependent Intrinsic Images for Video Surveillance", IEEE Transactions on Pattern Analysis and Machine Intelligence, vol. 26, Issue 10, Oct. 2004, pp. 1336-1347.
J. Davis et al., "An Adaptive Focus-of-Attention Model for Video Surveillance and Monitoring", Machine Vision and Application 18, 2007, pp. 41-64.
L. Herbert, "Othello Error: Facial Profiling, Privacy, and the Suppression of Dissent", Ohio State Journal of Criminal Law, vol. 5, 2007, pp. 79-129.
C. Larson et al., "The Shape of Threat: Simple Geometric Forms Evoke Rapid and Sustained Capture of Attention", Emotion 2007, vol. 7, No. 3, pp. 526-534.
A. Oredsson, "Cognitive Video Surveillance: An ANN/CBR Hybrid Approach", Master of Science in Informatics, Norwegian University of Science and Technology, Submitted Jun. 2007, pp. 1-136.
N. Siebel et al., "The Advisor Visual Surveillance System", Applications of Computer Vision '04, Prague, May 16, 2004, pp. 103-111.
U.S. Appl. No. 12/333,256, Prosecution History.
U.S. Appl. No. 12/333,273, Specification.
U.S. Appl. No. 12/333,319, Prosecution History.
U.S. Appl. No. 12/333,321, Prosecution History.
U.S. Appl. No. 12/333,326, Specification.
U.S. Appl. No. 12/335,521, Prosecution History.
U.S. Appl. No. 12/335,731, Specification.
U.S. Appl. No. 12/336,440, Prosecution History.
U.S. Appl. No. 12/336,488, Specification.
U.S. Appl. No. 12/335,857—Prosecution History.

Graham Center One-Pager, Types of Medical Errors Commonly Reported by Family Physicians, Am Fam Physician, Feb. 2003.
U.S. Appl. No. 12/333,311—Final Office Action, Aug. 18, 2011.
U.S. Appl. No. 12/333,316—Non-Final Office Action, Sep. 6, 2011.
U.S. Appl. No. 12/336,488—Non-Final Office Action, Sep. 15, 2011.
U.S. Appl. No. 12/275,830—Non-Final Office Action Mailed Dec. 14, 2011.
U.S. Appl. No. 12/335,521—Final Office Action Mailed Dec. 30, 2011.
Yalch et al., "The Effects of Music in a Retail Setting on Real and Perceived Shopping Times," Journal of Business Research 49, pp. 139-147, 2000.
U.S. Appl. No. 12/333,319—Final Office Action Mailed Feb. 1, 2012.
Gulas et al., "Right Under Our Noses: Ambient Scent and Consumer Responses," Journal of Business and Psychology, Fall 1995.
M. Bitner, "The Impact of Physical Surroundings on Customer and Employees," Journal of Marketing, Apr. 1992.
Knowledge@Wharton, Tag Team, "Tracking the Pattern of Supermarket Shoppers," Published Jun. 1, 2005.
Girgensohn et al., "Determining Activity Patterns in Retail Spaces Through Video Analysis," MM'08, Oct. 26-31, 2008.
U.S. Appl. No. 12/333,323—Notice of Allowance Mailed Nov. 15, 2011.
Lymberopoulos et al., "An Easy-To-Program Sensor System for Parsing Out Human Activities," Embedded Networks and Application Lab, ENALAB, Yale University, New Haven, CT, 2008, pp. 1-17.
U.S. Appl. No. 12/336,440—Final Office Action Mailed Feb. 27, 2012.
U.S. Appl. No. 12/336,488—Final Office Action Mailed Mar. 9, 2012.
U.S. Appl. No. 12/335,521—Examiner's Answer Mailed Apr. 25, 2012.
U.S. Appl. No. 12/335,857—Examiner's Answer Mailed Mar. 15, 2012.
U.S. Appl. No. 12/333,326—Non-Final Office Action Mailed May 16, 2012.
U.S. Appl. No. 12/333,273—Final Office Action Mailed May 23, 2012.
U.S. Appl. No. 12/336,488—Examiner's Answer Mailed Oct. 25, 2012.
U.S. Appl. No. 13/605,248—Non-Final Office Action Mailed Nov. 19, 2012.
U.S. Appl. No. 12/336,440—Examiner's Answer Mailed Nov. 23, 2012.
U.S. Appl. No. 12/333,321—Non-Final Office Action Mailed Dec. 19, 2012.
B. Welsh et al., "Effects of Improved Street Lighting on Crime," Sep. 24, 2008, Campbell Systematic Reviews. The Campbell Collaboration, pp. 1-54.
U.S. Appl. No. 12/333,273—Non-Final Office Action Mailed Jan. 31, 2013.
U.S. Appl. No. 12/333,256—Non-Final Office Action Mailed Feb. 14, 2013.
U.S. Appl. No. 12/333,311, Angell et al., Non-Final Office Action Mailed Jan. 24, 2012.
U.S. Appl. No. 12/333,311, Angell et al., Final Office Action Mailed Jun. 1, 2012.
U.S. Appl. No. 12/275,830, Angell et al.,—Notice of Allowance Mailed Jun. 25, 2012.

* cited by examiner

DESCRIPTION
DATA
600

```
INDIVIDUAL: JANE JONES
DRIVING HISTORY
        Number of Years Driving Experience: 16
        Number of Parking Tickets: 3
        Number of Traffic Tickets: 2
        No-fault Traffic Accidents: 1
        At-fault Traffic Accidents: 0
MEDICAL HISTORY
        Prescribed Antidepressants in 2002
EDUCATION
        Art History Degree
CURRENT STATUS
        Booked 2:00 flight to Paris
        Reserved tickets for Paris Art Museum Tour
```

FIG. 6

GENERATING DEPORTMENT AND COMPORTMENT COHORTS

BACKGROUND OF THE INVENTION

1. Field of the Invention

The present invention relates generally to an improved data processing system and in particular to a method and apparatus for generating cohorts. More particularly, the present invention is directed to a computer implemented method, apparatus, and computer usable program code for processing input in conduct analysis models to generate comportment and deportment cohorts.

2. Description of the Related Art

Psychology is the study of an individual's mental processes, conduct, and social behavior. Sociology is the study of an individual's conduct in social groups. Individuals may be the subjects of psychological and sociological studies that are used to understand and interpret the conduct, emotions, intentions, and tendencies of individuals to behave in a various ways in various situations. Subjects may be placed in cohorts for psychological or sociological study. A cohort is a group of people or animals that share a common attribute or experience. For example, a group of people born in 1980 may form a birth cohort. A cohort may include one or more sub-cohorts. For example, the birth cohort of people born in 1980 may include a sub-cohort of people born in 1980 in Salt Lake City, Utah. A sub-sub-cohort may include people born in 1980 in Dallas, Tex. to low income, single parent households. Cohorts are frequently generated based on one or more attributes of the members of each cohort. The information used to identify the attributes of members of a cohort is typically provided by the members of the cohort. However, information describing attributes of members of a cohort may be voluminous, dynamically changing, unavailable, difficult to collect, and/or unknown to the member of the cohort and/or the user selecting members of a cohort. Thus, unique cohorts may be suboptimal because individuals lack the skills, time, knowledge, and/or expertise needed to gather cohort attribute information from available sources.

BRIEF SUMMARY OF THE INVENTION

According to one embodiment of the present invention, a computer implemented method, apparatus, and computer program product for generating deportment and comportment cohorts is provided. Digital sensor data associated with an individual is received. The digital sensor data comprises event metadata describing a set of events associated with the individual. The set of events comprises at least one of body language, facial expressions, vocalizations, and social interactions of the individual. In response to determining description data for the individual is available, the description data is retrieved. The description data comprises at least one of identification information, past history information, and current status information for the individual. A set of conduct analysis models based on the event metadata and the available description data is selected. The set of conduct analysis models process the event metadata describing the set of events associated with the individual to identify and interpret the set of events. The event metadata and the description data is analyzed in the set of conduct analysis models to form a deportment and comportment cohort. The deportment and comportment cohort comprises attributes identifying a demeanor and manner of the individual.

BRIEF DESCRIPTION OF THE SEVERAL VIEWS OF THE DRAWINGS

FIG. 6 is a block diagram of description data for an individual in accordance with an illustrative embodiment.

DETAILED DESCRIPTION OF THE INVENTION

Figure 1:
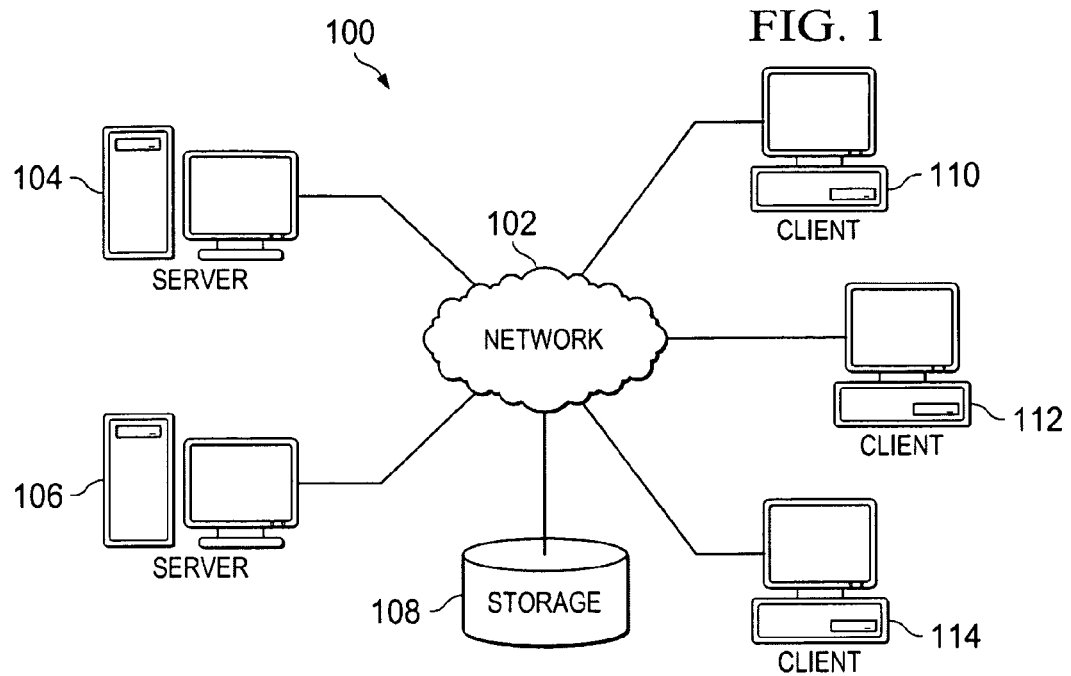
FIG. 1 is a pictorial representation of a network of data processing systems in which illustrative embodiments may be implemented.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wire line, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Figure 2:
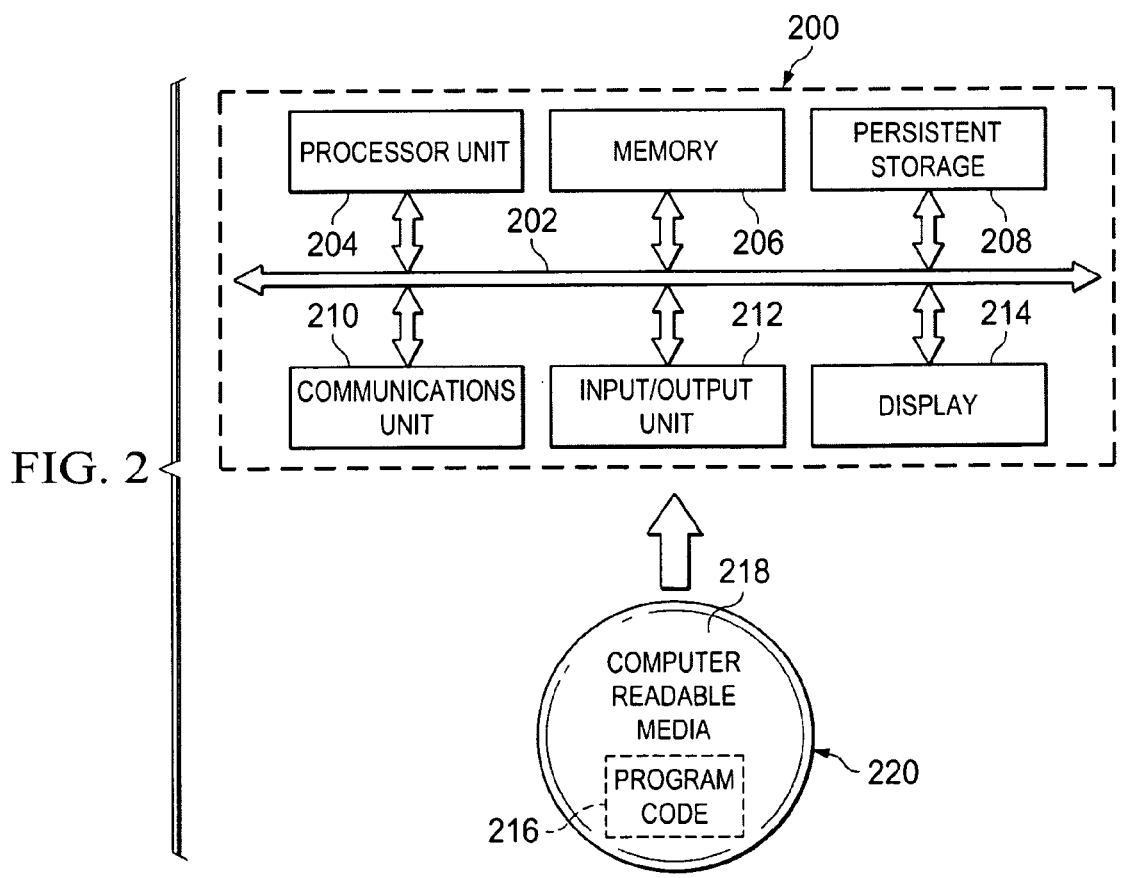
FIG. 2 is a block diagram of a data processing system in which illustrative embodiments may be implemented.

With reference now to the figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

Program code located in network data processing system 100 may be stored on a computer recordable storage medium and downloaded to a data processing system or other device for use. For example, program code may be stored on a computer recordable storage medium on server 104 and downloaded to client 110 over network 102 for use on client 110.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

With reference now to FIG. 2, a block diagram of a data processing system is shown in which illustrative embodiments may be implemented. Data processing system 200 is an example of a computer, such as, without limitation, server 104 or client 110 in FIG. 1, in which computer usable program code or instructions implementing the processes may be located for the illustrative embodiments. In this illustrative example, data processing system 200 includes communications fabric 202, which provides communications between processor unit 204; memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer recordable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

In some illustrative embodiments, program code 216 may be downloaded over a network to persistent storage 208 from another device or data processing system for use within data processing system 200. For instance, program code stored in a computer readable storage medium in a server data processing system may be downloaded over a network from the server to data processing system 200. The data processing system providing program code 216 may be a server computer, a client computer, or some other device capable of storing and transmitting program code 216.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown.

As one example, a storage device in data processing system 200 is any hardware apparatus that may store data. Memory 206, persistent storage 208, and computer readable media 218 are examples of storage devices in a tangible form.

In another example, a bus system may be used to implement communications fabric 202 and may be comprised of one or more buses, such as a system bus or input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. A memory may be, for example, memory 206 or a cache such as found in an interface and memory controller hub that may be present in communications fabric 202.

The illustrative embodiments recognize that the ability to quickly and accurately perform an assessment of a person's conduct to identify the person's demeanor, manner, emotional state, and other features of the person's conduct in different situations and circumstances may be valuable to business planning, hiring employees, health, safety, marketing, transportation, and various other industries. Thus, according to one embodiment of the present invention, a computer implemented method, apparatus, and computer program product for analyzing sensory input data and cohort data associated with a set of individuals to generate deportment and comportment cohorts is provided.

According to one embodiment of the present invention, a computer implemented method, apparatus, and computer program product for generating deportment and comportment cohorts is presented. Digital sensor data is received from a set of multimodal sensors associated with an individual. The digital sensor data comprises event metadata describing a set of events associated with the individual. The set of events comprises at least one of body language, facial expressions, vocalizations, and social interactions of the individual. In response to determining description data for the individual is available, the description data is retrieved. The description data comprises at least one of identification information, past history information, and current status information for the individual. A set of conduct analysis models based on the event metadata and the available description data is selected. The set of conduct analysis models process the event metadata describing the set of events associated with the individual to identify and interpret the set of events. The event metadata and the description data is analyzed in the set of conduct analysis models to form a deportment and comportment cohort. The deportment and comportment cohort comprises attributes identifying a demeanor and manner of the individual.

A cohort is a group of people or objects. Members of a cohort share a common attribute or experience in common. A cohort may be a member of a larger cohort. Likewise, a cohort may include members that are themselves cohorts, also referred to as sub-cohorts. In other words, a first cohort may include a group of members that forms a sub-cohort. That sub-cohort may also include a group of members that forms a sub-sub-cohort of the first cohort, and so on. A cohort may be a null set with no members, a set with a single member, as well as a set of members with two or more members.

Figure 3:
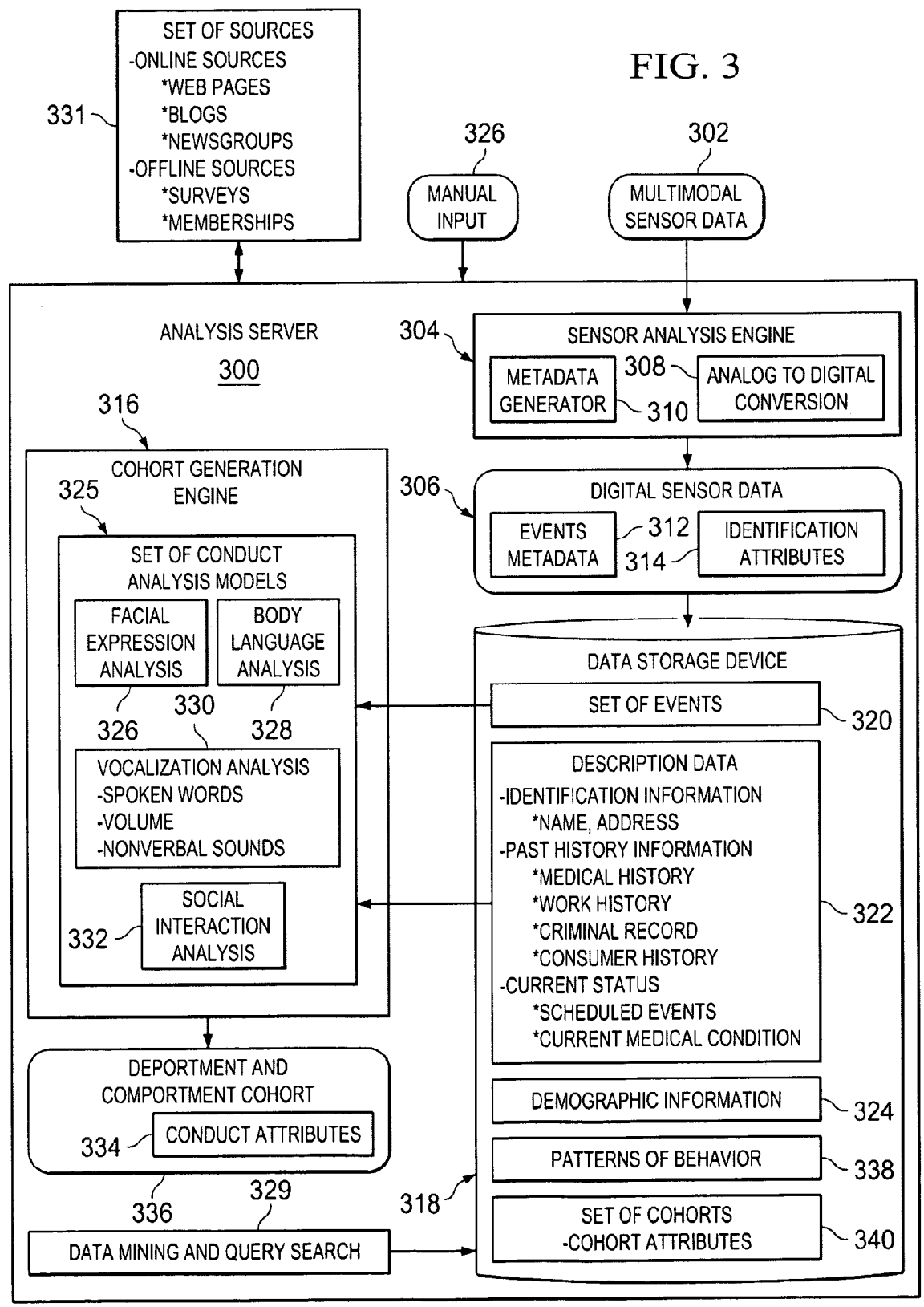
FIG. 3 is a block diagram of a conduct analysis system for generating deportment and comportment cohorts in accordance with an illustrative embodiment.

FIG. 3 is a block diagram of a conduct analysis system for generating deportment and comportment cohorts. Analysis server 300 is a server for analyzing sensor input associated with one or more individuals. Analysis server 300 may be implemented, without limitation, on a hardware computing device, such as, but not limited to, a main frame, server, a personal computer, laptop, personal digital assistant (PDA), or any other computing device depicted in FIGS. 1 and 2. Analysis server 300 receives multimodal sensor data 302 from a set of multimodal sensors. Multimodal sensor data is data that is received from a multimodal sensor. A multimodal sensor may be a camera, an audio device, a biometric sensor, a chemical sensor, or a sensor and actuator, such as set of multimodal sensors 400 in FIG. 4 below. Multimodal sensor data 302 is data that describes the set of individuals. In other words, multimodal sensors record readings for the set of individuals to form multimodal sensor data 302. For example, multimodal sensor data that is generated by a camera includes images of at least one individual in the set of individuals. As used herein, the term "at least one of", when used with a list of items, means that different combinations of one or more of the items may be used and only one of each item in the list may be needed. For example, "at least one of item A, item B, and item C" may include, for example, without limitation, item A alone, item B alone, item C alone, a combination of item A and item B, a combination of item B and item C, a combination of item A and item C, or a combination that includes item A, item B, and item C.

Multimodal sensor data that is generated by a microphone includes audio data of sounds made by at least one individual in the set of individuals. Thus, multimodal sensor data 310 may include, without limitation, sensor input in the form of audio data, images from a camera, biometric data, signals from sensors and actuators, and/or olfactory patterns from an artificial nose or other chemical sensor.

Sensor analysis engine 304 is software architecture for analyzing multimodal sensor data 302 to generate digital sensor data 306. Analog to digital conversion 308 is a software component that converts any multimodal sensor data that is in an analog format into a digital format. Analog to digital conversion 308 may be implemented using any known or available analog to digital converter (ADC). Sensor analysis engine 304 processes and parses the sensor data in the digital format to identify attributes of the set of individuals. Metadata generator 310 is a software component for generating metadata describing the identified attributes of the set of individuals.

Sensor analysis engine 304 may include a variety of software tools for processing and analyzing the different types of sensor data in multimodal sensor data 302. Sensor analysis engine 304 may include, without limitation, olfactory analytics for analyzing olfactory sensory data received from chemical sensors, video analytics for analyzing images received from cameras, audio analytics for analyzing audio data received from audio sensors, biometric data analytics for analyzing biometric sensor data from biometric sensors, and sensor and actuator signal analytics for analyzing sensor input data from sensors and actuators.

Sensor analysis engine 304 may be implemented using a variety of digital sensor analysis technologies, such as, without limitation, video image analysis technology, facial recognition technology, license plate recognition technology, and sound analysis technology. In one embodiment, sensor analysis engine 304 is implemented using, without limitation, IBM® smart surveillance system (S3) software.

Sensor analysis engine 304 utilizes computer vision and pattern recognition technologies, as well as video analytics to analyze video images captured by one or more situated cameras, microphones, or other multimodal sensors. The analysis of multimodal sensor data 302 generates events metadata 312 describing events of interest in the environment.

Sensor analysis engine 304 includes video analytics software for analyzing video images and audio files generated by the multimodal sensors. The video analytics may include, without limitation, behavior analysis, license plate recognition, face recognition, badge reader, and radar analytics technology. Behavior analysis technology tracks moving objects and classifies the objects into a number of predefined categories by analyzing metadata describing images captured by the cameras. As used herein, an object may be a human, an object, a container, a cart, a bicycle, a motorcycle, a car, a location, or an animal, such as, without limitation, a dog. License plate recognition may be utilized to analyze images captured by cameras deployed at the entrance to a facility, in a parking lot, on the side of a roadway or freeway, or at an intersection. License plate recognition catalogs a license plate of each vehicle moving within a range of two or more video cameras associated with sensor analysis engine 304. For example, license plate recognition technology may be utilized to identify a license plate number on license plate.

Face recognition is software for identifying a human based on an analysis of one or more images of the human's face. Face recognition technology may be utilized to analyze images of objects captured by cameras deployed at entryways, or any other location, to capture and recognize faces. Badge reader technology may be employed to read badges. The information associated with an object obtained from the badges is used in addition to video data associated with the object to identify an object and/or a direction, velocity, and/or acceleration of the object.

The data gathered from behavior analysis, license plate recognition, facial recognition, badge reader, radar analytics, and any other video/audio data received from a camera or other video/audio capture device is received by sensor analysis engine 304 for processing into events metadata 312 describing events and/or identification attributes 314 of one or more objects in a given area. The events from all these technologies are cross indexed into a common repository or a multi-mode event database allowing for correlation across multiple audio/video capture devices and event types. In such a repository, a simple time range query across the modalities will extract license plate information, vehicle appearance information, badge information, object location information, object position information, vehicle make, model, year and/or color, and face appearance information. This permits sensor analysis engine 304 to easily correlate these attributes.

Digital sensor data 306 comprises events metadata 312 describing set of events 320 associated with an individual in the set of individuals. An event is an action or event that is performed by the individual or in proximity to the individual. An event may be the individual making a sound, walking, eating, making a facial expression, a change in the individual's posture, spoken words, the individual throwing an object, talking to someone, carrying a child, holding hands with someone, picking up an object, standing still, or any other movement, conduct, or event.

Digital sensor data 306 may also optionally include identification attributes 314. An attribute is a characteristic, feature, or property of an object. An identification attribute is an attribute that may be used to identify a person. In a non-limiting example, identification attribute may include a person's name, address, eye color, age, voice pattern, color of their jacket, size of their shoes, retinal pattern, iris pattern, fingerprint, thumbprint, palm print, facial recognition data, badge reader data, smart card data, scent recognition data, license plate number, and so forth. Attributes of a thing may include the name of the thing, the value of the thing, whether the thing is moving or stationary, the size, height, volume, weight, color, or location of the thing, and any other property or characteristic of the thing.

Cohort generation engine 316 receives digital sensor data 306 from sensor analysis engine 304. Cohort generation engine 316 may request digital sensor data 306 from sensor analysis engine 304 or retrieve digital sensor data 306 from data storage device 318. In another embodiment, sensor analysis engine 304 automatically sends digital sensor data 306 to cohort generation engine 316 in real time as digital sensor data 306 is generated. In yet another embodiment, sensor analysis engine 304 sends digital sensor data 306 to cohort generation engine 316 upon the occurrence of a predetermined event. A predetermined event may be, but is not limited to, a given time, completion of processing multimodal sensor data 302, occurrence of a timeout event, a user request for generation of set of cohorts based on digital sensor data 306, or any other predetermined event. The illustrative embodiments may utilize digital sensor data 306 in real time as digital sensor data 306 is generated or utilize digital sensor data 306 that is pre-generated or stored in data storage device 318 until the digital sensor data is retrieved at some later time.

Data storage device 318 may be a local data storage located on the same computing device as cohort generation engine 316. In another embodiment, data storage device 318 is located on a remote data storage device that is accessed through a network connection. In yet another embodiment, data storage device 318 may be implemented using two or more data storage devices that may be either local or remote data storage devices.

Cohort generation engine 316 retrieves any description data 322 for the individual that is available. Description data 322 may include identification information identifying the individual, past history information for the individual, and/or current status information for the individual. Information identifying the individual may be a person's name, address, age, birth date, social security number, employee identification number, or any other identification information. Past history information is any information describing past events associated with the individual. Past history information may include medical history, work history/employment history, social security records, criminal record, consumer history, educational history, previous residences, prior owned property, repair history of property owned by the individual, or any other past history information. For example, education history may include, without limitation, schools attended, degrees obtained, grades earned, and so forth. Medical history may include previous medical conditions, previous medications prescribed to the individual, previous physicians that treated the individual, medical procedures/surgeries performed on the individual and any other past medical information.

Current status information is any information describing a current status of the individual. Current status information may include, for example and without limitation, scheduled events, current medical condition, current prescribed medications, current status of the individual's driver's license, current residence, marital status, and any other current status information.

Cohort generation engine 316 optionally retrieves demographic information 324 from data storage device 318. Demographic information 324 describes demographic data for the individual's demographic group. Demographic information 324 may be obtained from any source that compiles and distributes demographic information.

In another embodiment, cohort generation engine 316 receives manual input 326 that provides manual input describing the individual and/or manual input defining the analysis of events metadata 312 and/or identification attributes 314 for the individual.

In another embodiment, if description data 322 is not available, data mining and search query 329 searches set of sources 331 to identify additional description data for the individual. Set of sources 331 may include online sources, as well as offline sources. Online sources may be, without limitation, web pages, blogs, wikis, newsgroups, social networking sites, forums, online databases, and any other information available on the Internet. Off-line sources may include, without limitation, relational databases, data storage devices, or any other off-line source of information.

Cohort generation engine 316 selects a set of conduct analysis models for use in processing set of events 320, identification attributes 314, description data 322. demographic data 324, and/or manual input 326. Cohort generation engine 316 selects the conduct analysis models based on the type of event metadata and the available description data to form set of conduct analysis models 325. In this example, conduct analysis models may include, without limitation, facial expression analysis model 327, body language analysis model 328, vocalization analysis model 330, and social interaction analysis model 332.

Facial expression analysis model 327 analyzes images of an individual's face and generates conduct attributes 334 describing the individual's emotional state based on their expressions. For example, if a person is frowning and their brow is furrowed, facial expression analysis model 327 may infer that the person is angry or annoyed. If the person is pressing their lips together and shuffling their feet, the person may be feeling uncertain or pensive. These emotions are identified in conduct attributes 334. Body language analysis model 328 analyzes images of a person's body motions and movements, as well as other attributes indicating movements of the person's feet, hands, posture, hands, and arms to identify conduct attributes describing the person's manner, attitude, and conduct.

Vocalization analysis model 330 analyzes set of events 320, identification attributes 314, and description data 322 to identify sounds made by the individual and words spoken by the individual. Vocalizations may include, words spoken, volume of sounds, and non-verbal sounds. For example, and without limitation, vocalization analysis model 330 identifies cries, shouts, clicking, whistling, humming, popping sounds, the volume of a shout or cry, and other sounds made by a person. Social interaction analysis model 332 analyzes set of events 320 and demographic data 322 to identify appropriate and inappropriate social interactions. Social interactions are the verbal and physical interactions of a person with one or more other people and/or animals. For example, but without limitation, social interactions may include shaking hands, striking a person, a verbal greeting, a hug, a kiss, or any other type of interaction. Social interactions may also identify a person avoiding social contact with others.

Cohort generation engine 316 selects analysis models for set of conduct analysis models 325 based on the type of events in set of events and the type of description data available. For example, if the set of events and identification attributes includes video data of the individual's face and facial expressions, cohort generation engine 316 may select facial expression analysis model 327 to analyze set of events 320. If set of events 322 includes video images of the individual's body movements, posture, arm movements, hand gestures and finger motions, foot movements, or other body motions, cohort generation engine 316 may select body language analysis model 328 to process set of events 320.

Cohort generation engine 316 analyzes events metadata 312 describing set of events 320 and identification attributes 314 with any demographic information 324, description data 322, and/or user input 326 in the selected set of conduct analysis models 325 to form deportment and comportment cohort 336. Deportment and comportment cohort 336 may include a sociologic cohort, a deportment cohort and/or a comportment cohort. Deportment refers to the way a person behaves toward other people, demeanor, conduct, behavior, manners, social deportment, citizenship, swashbuckling, correctitude, properness, propriety, improperness, impropriety, and personal manner. Swashbuckling refers to flamboyant, reckless, or boastful behavior. The deportment cohort may identify conduct attributes 334 indicating the type of demeanor, manner, or conduct being displaying.

The term comportment refers to how refined or unrefined the person's overall manner appears. The comportment cohort may include conduct attributes 334 identifying whether the persons overall behavior is refined, smooth, or confident. The comportment cohort may also indicate if the person's overall behavior is rough, uncertain, hesitant, unrefined, or otherwise how well the person is able to complete tasks.

The term sociologic refers to social manner, social interactions, and the manner in which the person interacts with other people and with animals. The sociologic cohort may indicate whether a person is a leader, a follower, a loner, an introvert, an extrovert, a manipulator or charismatic personality, as well as other social interactive traits.

In another embodiment, cohort generation engine 316 compares conduct attributes 334 to patterns of conduct 338 to identify additional members of deportment and comportment cohort 336. Patterns of conduct 338 are known patterns of conduct that indicate a particular demeanor, attitude, emotional state, or manner of a person. Each different type of conduct by an individual in different environments results in different sensor data patterns and different attributes. When a match is formed between known patterns of conduct 338 and some of conduct attributes 334, the matching pattern may be used to identify attributes and conduct of the individual.

In yet another embodiment, cohort generation engine 316 also retrieves set of cohorts 340. Set of cohorts 340 is a set of one or more cohorts associated with the individual. Set of cohorts 340 may include an audio cohort, a video cohort, a biometric cohort, a furtive glance cohort, a sensor and actuator cohort, specific risk cohort, a general risk cohort, a predilection cohort, and/or an olfactory cohort. Cohort generation engine 316 optionally analyzes cohort data and attributes of cohorts in set of cohorts 340 with set of events 320, description data 322, and identification attributes 314 in set of conduct analysis models 325 to generate deportment and comportment cohort 336.

In response to new digital sensor data being generated by sensor analysis engine 304, cohort generation engine 316 analyzes the new digital sensor data in set of conduct analysis models 325 to generate an updated set of events and an updated deportment and comportment cohort.

Figure 4:
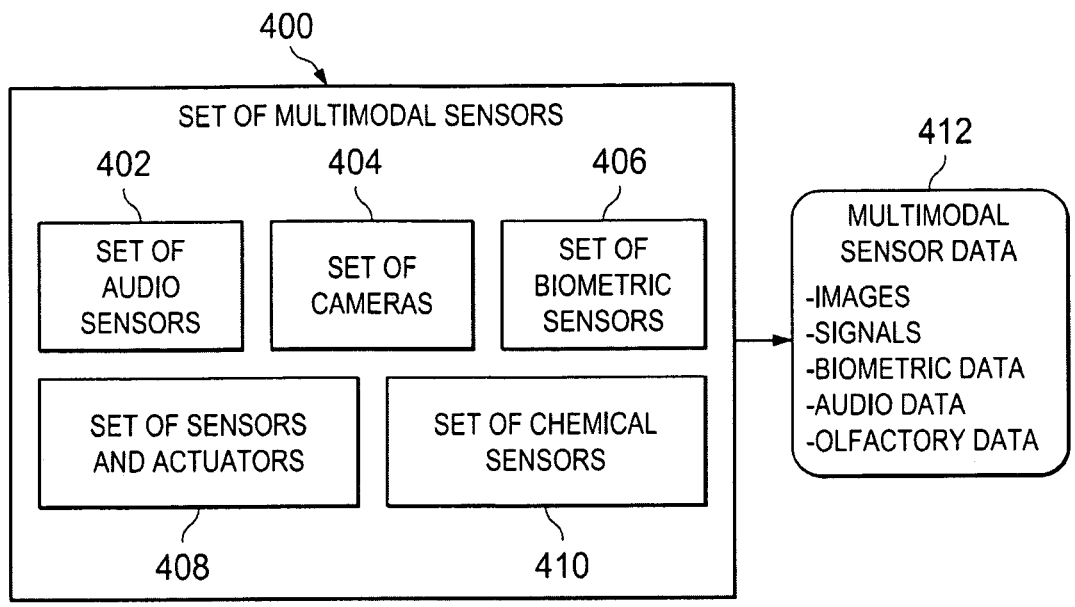
FIG. 4 is a block diagram of a set of multimodal sensors in accordance with an illustrative embodiment.

Referring now to FIG. 4, a block diagram of a set of multimodal sensors is depicted in accordance with an illustrative embodiment. Set of multimodal sensors 400 is a set of sensors that gather sensor data associated with a set of individuals. In this non-limiting example, set of multimodal sensors 400 includes set of audio sensors 402, set of cameras 404, set of biometric sensors 406, set of sensors and actuators 408, set of chemical sensors 410, and any other types of devices for gathering data associated with a set of objects and transmitting that data to an analysis engine, such as sensor analysis engine 304 in FIG. 3. Set of multimodal sensors 400 detect, capture, and/or record multimodal sensor data 412.

Set of audio sensors 402 is a set of audio input devices that detect, capture, and/or record vibrations, such as, without limitation, pressure waves, and sound waves. Vibrations may be detected as the vibrations are transmitted through any medium, such as, a solid object, a liquid, a semisolid, or a gas, such as the air or atmosphere. Set of audio sensors 402 may include only a single audio input device, as well as two or more audio input devices. An audio sensor in set of audio sensors 402 may be implemented as any type of device that can detect vibrations transmitted through a medium, such as, without limitation, a microphone, a sonar device, an acoustic identification system, or any other device capable of detecting vibrations transmitted through a medium.

Set of cameras 404 may be implemented as any type of known or available camera(s). A cameral may be, without limitation, a video camera for generating moving video images, a digital camera capable of taking still pictures and/or a continuous video stream, a stereo camera, a web camera, and/or any other imaging device capable of capturing a view of whatever appears within the camera's range for remote monitoring, viewing, or recording of an object or area. Various lenses, filters, and other optical devices such as zoom lenses, wide-angle lenses, mirrors, prisms, and the like, may also be used with set of cameras 404 to assist in capturing the desired view. A camera may be fixed in a particular orientation and configuration, or it may, along with any optical devices, be programmable in orientation, light sensitivity level, focus or other parameters.

Set of cameras 404 may be implemented as a stationary camera and/or non-stationary camera. A stationary camera is in a fixed location. A non-stationary camera may be capable of moving from one location to another location. Stationary and non-stationary cameras may be capable of tilting up, down, left, and right, panning, and/or rotating about an axis of rotation to follow or track an object in motion or keep the object, within a viewing range of the camera lens. The image and/or audio data in multimodal sensor data 412 that is generated by set of cameras 404 may be a sound file, a media file, a moving video file, a still picture, a set of still pictures, or any other form of image data and/or audio data. Video and/or audio data 404 may include, for example and without limitation, images of a person's face, an image of a part or portion of a customer's car, an image of a license plate on a car, and/or one or more images showing a person's behavior. In a non-limiting example, an image showing a customer's behavior or appearance may show a customer wearing a long coat on a hot day, a customer walking with two small children, a customer moving in a hurried or leisurely manner, or any other type behavior of one or more objects.

Set of biometric sensors 406 is a set of one or more devices for gathering biometric data associated with a human or an animal. Biometric data is data describing a physiological state, physical attribute, or measurement of a physiological condition. Biometric data may include, without limitation, fingerprints, thumbprints, palm prints, footprints, hear rate, retinal patterns, iris patterns, pupil dilation, blood pressure, respiratory rate, body temperature, blood sugar levels, and any other physiological data. Set of biometric sensors 406 may include, without limitation, fingerprint scanners, palm scanners, thumb print scanners, retinal scanners, iris scanners, wireless blood pressure monitor, heart monitor, thermometer or other body temperature measurement device, blood sugar monitor, microphone capable of detecting heart beats and/or breath sounds, a breathalyzer, or any other type of biometric device.

Set of sensors and actuators 408 is a set of devices for detecting and receiving signals from devices transmitting signals associated with the set of objects. Set of sensors and actuators 408 may include, without limitation, radio frequency identification (RFID) tag readers, global positioning system (GPS) receivers, identification code readers, network devices, and proximity card readers. A network device is a wireless transmission device that may include a wireless personal area network (PAN), a wireless network connection, a radio transmitter, a cellular telephone, Wi-Fi technology, Bluetooth technology, or any other wired or wireless device for transmitting and receiving data. An identification code reader may be, without limitation, a bar code reader, a dot code reader, a universal product code (UPC) reader, an optical character recognition (OCR) text reader, or any other type of identification code reader. A GPS receiver may be located in an object, such as a car, a portable navigation system, a personal digital assistant (PDA), a cellular telephone, or any other type of object.

Set of chemical sensors 410 may be implemented as any type of known or available device that can detect airborne chemicals and/or airborne odor causing elements, molecules, gases, compounds, and/or combinations of molecules, elements, gases, and/or compounds in an air sample, such as, without limitation, an airborne chemical sensor, a gas detector, and/or an electronic nose. In one embodiment, set of chemical sensors 410 is implemented as an array of electronic olfactory sensors and a pattern recognition system that detects and recognizes odors and identifies olfactory patterns associated with different odor causing particles. The array of electronic olfactory sensors may include, without limitation, metal oxide semiconductors (MOS), conducting polymers (CP), quartz crystal microbalance, surface acoustic wave (SAW), and field effect transistors (MOSFET). The particles detected by set of chemical sensors may include, without limitation, atoms, molecules, elements, gases, compounds, or any type of airborne odor causing matter. Set of chemical sensors 410 detects the particles in the air sample and generates olfactory pattern data in multimodal sensor data 412.

Multimodal sensor data 412 may be in an analog format, in a digital format, or some of the multimodal sensor data may be in analog format while other multimodal sensor data may be in digital format.

Figure 5:
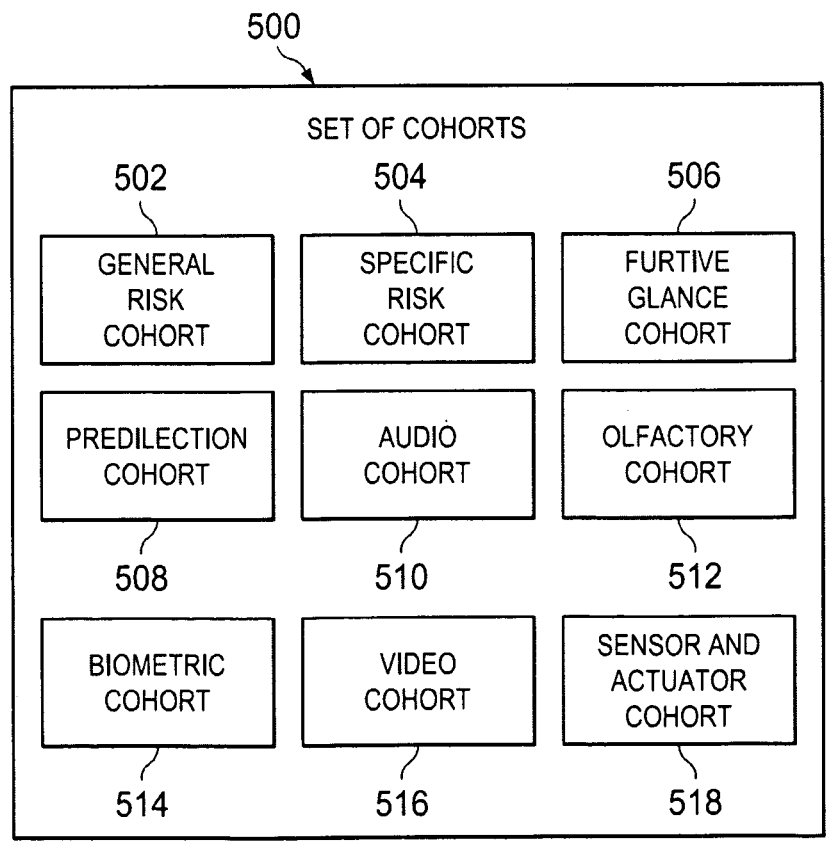
FIG. 5 is a diagram of a set of cohorts used to generate a deportment and comportment cohort in accordance with an illustrative embodiment.

FIG. 5 is a block diagram of a set of cohorts used to generate a deportment and comportment cohort in accordance with an illustrative embodiment. Set of cohorts 500 is a set of one or more cohorts associated with a set of individuals, such as set of cohorts 340 in FIG. 3. General risk cohort 502 is a cohort having members that are general or generic rather than specific. Each member of general risk cohort 502 comprises data describing objects belonging to a category. A category refers to a class, group, category, or kind. A member of a general cohort is a category or sub-cohort including general or average and the risks associated with those members. Specific risk cohort 504 is a cohort having members that are specific, identifiable individuals and the risks associated with the members of the cohort. Furtive glance cohort 506 is a cohort comprising attributes describing eye movements by members of the cohort. The furtive glance attributes describe eye movements, such as, but without limitation, furtive, rapidly shifting eye movements, rapid blinking, fixed stare, failure to blink, rate of blinking, length of a fixed stare, pupil dilations, or other eye movements.

A predilection is the tendency or inclination to take an action or refrain from taking an action. Predilection cohort 508 comprises attributes indicating whether an identified person will engage in or perform a particular action given a particular set of circumstances. Audio cohort 510 is a cohort comprising a set of members associated with attributes identifying a sound, a type of sound, a source or origin of a sound, identifying an object generating a sound, identifying a combination of sounds, identifying a combination of objects generating a sound or a combination of sounds, a volume of a sound, and sound wave properties.

Olfactory cohort 512 is a cohort comprising a set of members associated with attributes a chemical composition of gases and/or compounds in the air sample, a rate of change of the chemical composition of the air sample over time, an origin of gases in the air sample, an identification of gases in the air sample, an identification of odor causing compounds in the air sample, an identification of elements or constituent gases in the air sample, an identification of chemical properties and/or chemical reactivity of elements and/or compounds in the air sample, or any other attributes of particles into the air sample.

Biometric cohort 514 is a set of members that share at least one biometric attribute in common. A biometric attribute is an attribute describing a physiologic change or physiologic attribute of a person, such as, without limitation, heart rate, blood pressure, finger print, thumb print, palm print, retinal pattern, iris pattern, blood type, respiratory rate, blood sugar level, body temperature, or any other biometric data.

Video cohort 516 is a cohort having a set of members associated with video attributes. Video attributes may include, without limitation, a description of a person's face, color of an object, texture of a surface of an object, size, height, weight, volume, shape, length, width, or any other visible features of the cohort member.

Sensor and actuator cohort 518 includes a set of members associated with attributes describing signals received from sensors or actuators. An actuator is a device for moving or controlling a mechanism. A sensor is a device that gathers information describing a condition, such as, without limitation, temperature, pressure, speed, position, and/or other data. A sensor and/or actuator may include, without limitation, a bar code reader, an electronic product code reader, a radio frequency identification (RFID) reader, oxygen sensors, temperature sensors, pressure sensors, a global positioning system (GPS) receiver, also referred to as a global navigation satellite system receiver, Bluetooth, wireless blood pressure monitor, personal digital assistant (PDA), a cellular telephone, or any other type of sensor or actuator.

FIG. 6 is a block diagram of description data for an individual in accordance with an illustrative embodiment. Description data 600 is data comprising identification data, past history information, and current status information for an individual, such as description data 322 in FIG. 3. In this example, description data include the individual name, driving history, medical history, educational history, and current status information for a planned trip to France. The embodiments are not limited to this description data or this type of description data. The embodiments may be implemented with any type of pre-generated information describing events associated with the individual's current status and/or past history.

Figure 7:
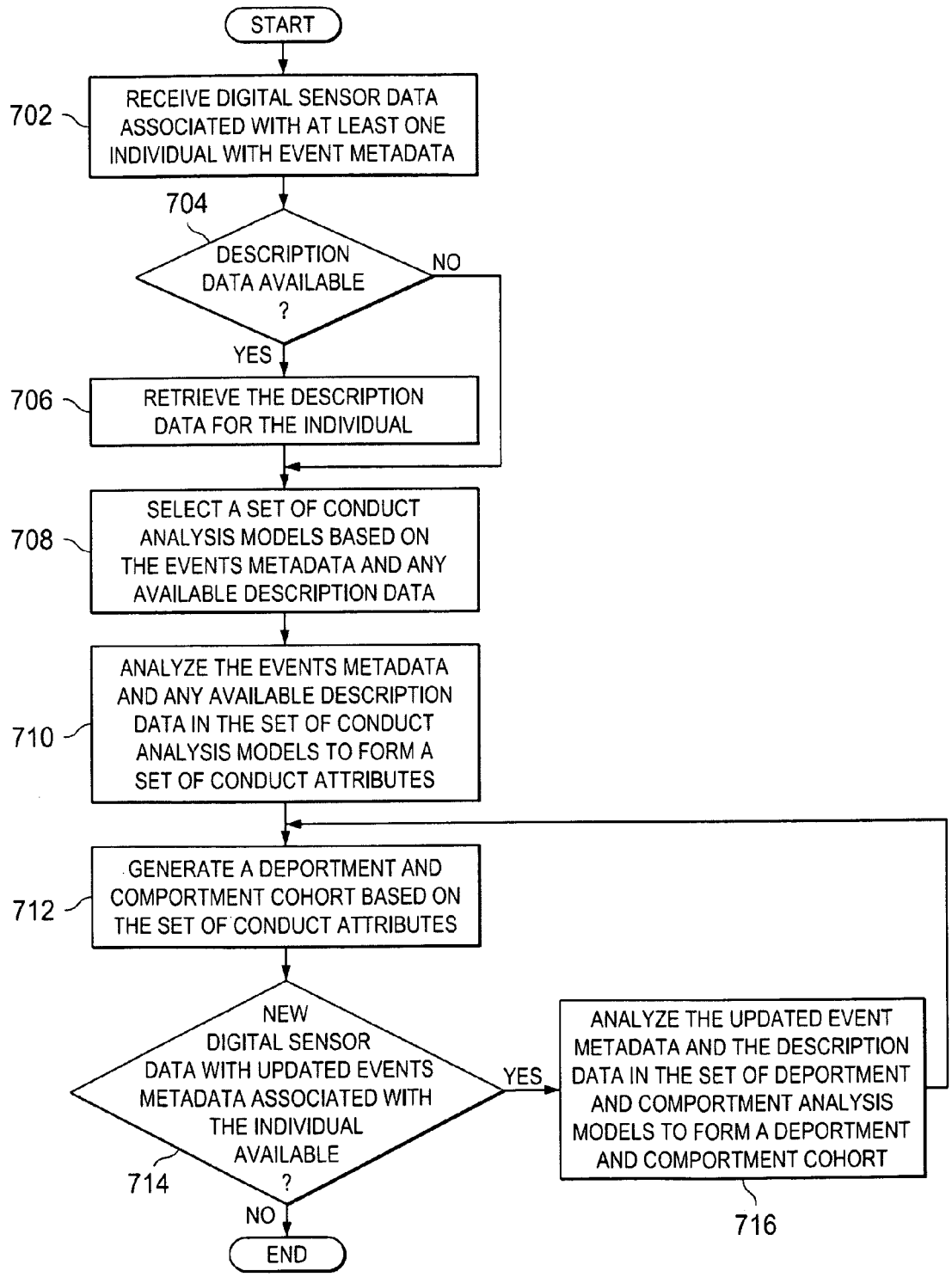
FIG. 7 is a flowchart of a process for generating a deportment and comportment cohort in accordance with an illustrative embodiment.

Turning now to FIG. 7, a flowchart of a process for generating a deportment and comportment cohort is shown in accordance with an illustrative embodiment. The process in FIG. 7 may be implemented by software for generating a cohort using deportment and comportment analysis models, such as cohort generation engine 316 in FIG. 3. The process begins by receiving digital sensor data associated with at least one individual from a sensor analysis engine (step 702). The digital sensor data includes events metadata. The process makes a determination as to whether description data is available (step 704). If description data is available, the process retrieves the description data for the individual (step 706). The process selects a set of conduct analysis models based on the events metadata and any available description data (step 708). The process analyzes the events metadata and any available description data in the set of conduct analysis models to form a set of conduct attributes (step 710). The process generates a deportment and comportment cohort based on the set of conduct attributes (step 712).

The process then makes a determination as to whether any new digital sensor data with updated events metadata for the individual is available (step 714). If no new digital sensor data is available, the process terminates thereafter. If new digital sensor data is available at step 712, the process analyzes the updated event metadata and the description data in the set of deportment and comportment analysis models to form an updated comportment and deportment cohort (step 716) with the process terminating thereafter.

Thus, according to one embodiment of the present invention, a computer implemented method, apparatus, and computer program product for generating deportment and comportment cohorts is provided. Digital sensor data is received from a set of multimodal sensors associated with an individual. The digital sensor data comprises event metadata describing a set of events associated with the individual. The set of events comprises at least one of body language, facial expressions, vocalizations, and social interactions of the individual. In response to determining description data for the individual is available, the description data is retrieved. The description data comprises at least one of identification information, past history information, and current status information for the individual. A set of conduct analysis models based on the event metadata and the available description data is selected. The set of conduct analysis models process the event metadata describing the set of events associated with the individual to identify and interpret the set of events. The event metadata and the description data is analyzed in the set of conduct analysis models to form a deportment and comportment cohort. The deportment and comportment cohort comprises attributes identifying a demeanor and manner of the individual.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method of generating deportment and comportment cohorts, the computer implemented method comprising:

receiving digital sensor data associated with an individual, wherein the digital sensor data comprises event metadata describing a set of events associated with the individual, wherein the set of events comprises at least one of body language, facial expressions, and vocalizations of the individual;

responsive to determining description data for the individual is available, retrieving the description data, wherein the description data comprises identification information, past activity history information, and current activity status information for the individual, and wherein the past activity history information describes a medical history of the individual;

selecting a set of conduct analysis models based on the event metadata and the available description data, wherein the set of conduct analysis models process the event metadata describing the set of events associated with the individual to identify and interpret the set of events; and analyzing the event metadata and the description data in the set of conduct analysis models to form a deportment and comportment cohort, wherein the deportment and comportment cohort comprises attributes identifying a demeanor and manner of the individual.

2. The computer implemented method of claim 1, wherein the digital sensor data comprises attribute metadata describing identification attributes of the individual, wherein the event metadata, attribute metadata, and the description data are analyzed in the set of conduct analysis models to form the deportment and comportment cohort, wherein an identification attribute is selected from a group consisting of a fingerprint, a thumbprint, a palm print, a voice pattern, a retinal scan result, an iris scan result, facial recognition, badge reader data, smart card data, a scent recognition, and license plate information.

3. The computer implemented method of claim 1, wherein the deportment and comportment cohort comprises a deportment sub-cohort, and wherein the deportment sub-cohort comprises attributes indicating at least one of a demeanor, conduct, manner, social deportment, propriety, impropriety, and flamboyant actions of the individual.

4. The computer implemented method of claim 1, wherein the digital sensor data is received from a set of multimodal sensors, wherein the set of multimodal sensors comprises a set of chemical sensors, a set of audio sensors, a set of cameras, a set of biometric sensors, and a set of sensors and actuators, wherein the biometric sensors detect a physiological condition of the individual, and wherein the computer implemented method further comprises:

responsive to receiving sensor data from the set of multimodal sensors in an analog format, processing the sensor data to convert the sensor data from the analog format into a digital format to form the digital sensor data.

5. The computer implemented method of claim 1, wherein the set of events further comprises social interactions between the individual and other observed persons.

6. The computer implemented method of claim 1, wherein the past activity history information further describes an education history and a work history of the individual.

7. The computer implemented method of claim 1, wherein the deportment and comportment cohort comprises a sociological sub-cohort, wherein the sociological sub-cohort comprises members having attributes indicating type of social interactions engaged in by the individual and a level of appropriateness of the social interactions.

8. The computer implemented method of claim further comprising:

responsive to a determination that new digital sensor data associated with the individual is available, receiving the new digital sensor data, wherein the new digital sensor data comprises updated event metadata describing a new set of events associated with the individual;

analyzing the updated event metadata with the description data in the set of conduct analysis models to generate an updated result.

9. The computer implemented method of claim 1, wherein the set of conduct analysis models comprise a set of psychological and sociological models, and wherein the computer implemented method further comprises:

responsive to receiving cohort data for a set of cohorts associated with the individual, selecting an updated set of psychological and sociological models to create an updated set of conduct analysis models; and analyzing the cohort data with the event metadata in the updated set of conduct analysis models to generate an updated result.

10. The computer implemented method of claim 1, wherein the current activity status information describes a current medical condition and scheduled events for the individual.

11. A computer program product for generating deportment and comportment cohorts, the computer program product comprising:

a non-transitory computer usable medium having computer usable program code embodied therewith, the computer usable program code comprising:

computer usable program code configured to receive digital sensor data associated with an individual, wherein the digital sensor data comprises event metadata describing a set of events associated with the individual, wherein the set of events comprises body language, facial expressions, vocalizations, and social interactions of the individual;

computer usable program code configured to retrieve description data in response to determining the description data for the individual is available, wherein the description data comprises identification information, past history information, and current status information for the individual;

computer usable program code configured to select a set of conduct analysis models based on the event metadata and the available description data, wherein the set of conduct analysis models process the event metadata describing the set of events associated with the individual to identify and interpret the set of events; and computer usable program code configured to analyze the event metadata and the description data in the set of conduct analysis models to form a deportment and comportment cohort, wherein the deportment and comportment cohort comprises attributes identifying a demeanor and manner of the individual.

12. The computer program product of claim 11, wherein the deportment and comportment cohort comprises a deportment sub-cohort, and wherein the deportment sub-cohort comprises attributes indicating at least one of a demeanor, conduct, manner, social deportment, propriety, impropriety, and flamboyant actions of the individual.

13. The computer program product of claim 11, wherein the deportment and comportment cohort comprises a deportment cohort, wherein the deportment cohort comprises attributes identifying an emotional state of the individual, wherein the emotional state comprises at least one of fear, joy, happiness, anger, jealousy, embarrassment, depression, and unemotional.

14. The computer program product of claim 11, wherein the comportment and deportment cohort comprises a comportment cohort, wherein the comportment cohort comprises attributes indicating an overall level of refinement in movements made by the individual.

15. The computer program product of claim 11, wherein the deportment and comportment cohort comprises a sociological sub-cohort, wherein the sociological sub-cohort comprises members having attributes indicating type of social interactions engaged in by the individual and a level of appropriateness of the social interactions.

16. An apparatus comprising:
a bus system;
a communications system coupled to the bus system;
a memory connected to the bus system, wherein the memory includes computer usable program code; and
a processing unit coupled to the bus system, wherein the processing unit executes the computer usable program code to receive digital sensor data associated with an individual, wherein the digital sensor data comprises event metadata describing a set of events associated with the individual, wherein the set of events comprises body language, facial expressions, vocalizations, and social interactions of the individual; retrieve description data in response to determining the description data for the individual is available, wherein the description data comprises identification information, past history information, and current status information for the individual; select a set of conduct analysis models based on the event metadata and the available description data, wherein the set of conduct analysis models process the event metadata describing the set of events associated with the individual to identify and interpret the set of events; and analyze the event metadata and the description data in the set of conduct analysis models to form a deportment and comportment cohort, wherein the deportment and comportment cohort comprises attributes identifying a demeanor and manner of the individual.

17. The apparatus of claim 16, wherein the deportment and comportment cohort comprises a deportment sub-cohort, and wherein the deportment sub-cohort comprises attributes indicating at least one of a demeanor, conduct, manner, social deportment, propriety, impropriety, and flamboyant actions of the individual.

18. The apparatus of claim 16, wherein the comportment and deportment cohort comprises a comportment cohort, wherein the comportment cohort comprises attributes indicating an overall level of refinement in movements made by the individual.

19. The apparatus of claim 16, wherein the deportment and comportment cohort comprises a sociological sub-cohort, wherein the sociological sub-cohort comprises members having attributes indicating type of social interactions engaged in by the individual and a level of appropriateness of the social interactions.

20. A conduct analysis system comprising:
a set of multimodal sensors, wherein the set of multimodal sensors generates multimodal sensor data associated with a set of individuals; and
an analysis server, wherein the analysis server receives digital sensor data associated with an individual, wherein the digital sensor data comprises event metadata describing a set of events associated with the individual, wherein the set of events comprises body language, facial expressions, vocalizations, and social interactions of the individual; and retrieves description data in response to determining the description data for the individual is available, wherein the description data comprises identification information, past history information, and current status information for the individual; and wherein the analysis server comprises:
a cohort generation engine, wherein the cohort generation engine selects a set of conduct analysis models based on the event metadata and the available description data, wherein the set of conduct analysis models process the event metadata describing the set of events associated with the individual to identify and interpret the set of events; and analyzes the event metadata and the description data in the set of conduct analysis models to form a deportment and comportment cohort, wherein the deportment and comportment cohort comprises attributes identifying a demeanor and manner of the individual.

* * * * *